(12) United States Patent
Murata et al.

(10) Patent No.: US 7,781,612 B2
(45) Date of Patent: *Aug. 24, 2010

(54) PROCESS FOR PRODUCING FLUORINATED SULFONYL FLUORIDE

(75) Inventors: Koichi Murata, Yokohama (JP); Takashi Okazoe, Yokohama (JP); Eisuke Murotani, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 1273 days.

This patent is subject to a terminal disclaimer.

(21) Appl. No.: 11/318,978

(22) Filed: Dec. 28, 2005

(65) Prior Publication Data

US 2006/0111584 A1    May 25, 2006

Related U.S. Application Data

(63) Continuation of application No. PCT/JP2004/009769, filed on Jul. 2, 2004.

(30) Foreign Application Priority Data

Jul. 4, 2003    (JP)    ............................. 2003-271071

(51) Int. Cl.
     *C07C 303/02*    (2006.01)

(52) U.S. Cl. ..................... 562/821; 562/825; 562/835

(58) Field of Classification Search ................ 562/821, 562/825, 835

See application file for complete search history.

(56) References Cited

U.S. PATENT DOCUMENTS

| | | | |
|---|---|---|---|
| 4,510,328 | A | 4/1985 | Kimoto et al. |
| 4,511,518 | A | 4/1985 | Kimoto et al. |
| 4,536,352 | A | 8/1985 | Kimoto et al. |
| 5,093,432 | A | 3/1992 | Bierschenk et al. |
| 5,466,877 | A | 11/1995 | Moore |
| 5,491,145 | A | 2/1996 | Miyake et al. |
| 6,790,982 | B2 | 9/2004 | Ito et al. |
| 2004/0181091 | A1 | 9/2004 | Ito et al. |

FOREIGN PATENT DOCUMENTS

| | | |
|---|---|---|
| AO | 02/44138 | 6/2002 |
| AP | 60/36454 | 2/1985 |
| EP | 1346980 * | 9/2003 |
| GB | 2 118 541 A | 11/1983 |
| JP | 56-92263 | 7/1981 |
| RU | 1230464 | 5/1986 |
| WO | 98/43952 | 10/1998 |
| WO | 03/002506 | 1/2003 |
| WO | 2004/094365 | 4/2004 |

OTHER PUBLICATIONS

U.S. Appl. No. 11/322,396, filed Jan. 3, 2006, Murata, et al.
Masaaki Kuwahara, et al., "Synthetic Studies on Condensed-Azole Derivatives. IV. Synthesis and Anti-asthmatic Activities of ω-Sulfamoylalkyloxyimidazo[1,2-b]pyridazines", Chem. Pharm. Bull., vol. 44, No. 1, XP-002204237, 1996, pp. 122-131.
Gramstad, T., et al., "Perfluoroalkyl Derivatives of Sulphur. Part IV.* Perfluoroalkanesulphonic Acids," Chem. Soc., 1956, pp. 173-180.
Hiyama, T., et al., Organofluorine Compounds, Chemistry and Applications, Springer-Verlag, Berlin, 2000, pp. 228-230.
Scott, Robert B., et al., "A Study of Aliphatic Sulfonyl Compounds IV. Neopenthylmethanesulfonyl Chloride," The Journal of Organic Chemistry, vol. 21, No. 4, Apr. 30, 1956, pp. 385-387.

* cited by examiner

*Primary Examiner*—Peter G O'Sullivan
(74) *Attorney, Agent, or Firm*—Oblon, Spivak, McClelland, Maier & Neustadt, L.L.P.

(57) ABSTRACT

The present invention provides a process for producing a fluorinated sulfonyl fluoride useful as e.g. a material for an ion exchange resin, and a novel chemical substance useful as an intermediate in the production process.

That is, to provide a process comprising oxidizing Y—S—$R^A$-E-$R^B$ by means of an oxidizing agent essentially containing a halogen atom to obtain $XSO_2$—$R^A$-E-$R^B$, and in a case that X is a fluorine atom, reacting the compound with fluorine in a liquid phase as it is, and in a case that X is a halogen atom other than a fluorine atom, converting X into a fluorine atom, and then reacting the obtained compound with fluorine in a liquid phase to obtain $FSO_2$—$R^{AF}$-$E^F$-$R^{BF}$, and then decomposing it to obtain $FSO_2$—$R^{AF}$—COF (wherein $R^A$ is a bivalent organic group such as an alkylene group, $R^B$ is a monovalent organic group such as a perfluoroalkyl group, E is —$CH_2OCO$—, Y is a monovalent organic group such as a cyano group or the like, X is a halogen atom, $R^{AF}$ is a bivalent organic group having $R^A$ fluorinated or the like, $R^{BF}$ is the same group as $R^B$ or the like, and $E^F$ is —$CF_2OCO$—).

10 Claims, No Drawings

PROCESS FOR PRODUCING FLUORINATED SULFONYL FLUORIDE

TECHNICAL FIELD

The present invention relates to a process for producing fluorinated sulfonyl fluorides useful as e.g. materials for ion-exchange resins, and novel chemical substances useful as intermediates in the process.

BACKGROUND ART

Fluorinated sulfonyl fluorides having a fluoroformyl group are compounds useful as materials for ion-exchange resins. As a process for producing such compounds, there is a process of reacting a perfluoroalkylene oxide with a cyclic compound obtainable by a reaction of tetrafluoroethylene with sulfur trioxide ($SO_3$) represented by the following scheme (the following scheme and Organofluorine Compounds, Chemistry and Applications, T. Hiyama et al., Springer-Verlag, Berlin, 2000, pages 228 to 230):

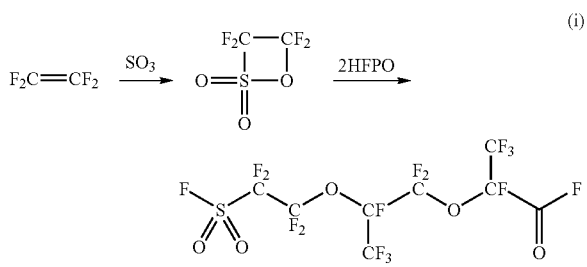

(i)

However, the conventional process is a disadvantageous process for practical industrial application, since due care is required for handling $SO_3$. Further, the process is economically disadvantageous because the difficulty in synthesis is high. In addition, the reaction product is limited to a compound having a side chain (such as a —$CF_3$ group), whereby there is a problem from the viewpoint of the performance and the membrane characteristics of an ion-exchange membrane.

As a process to solve the above problems, the following process is proposed (WO02/44138) wherein a hydrocarbon sulfonic acid derivative having a hydroxyl group is converted into an ester with a fluorinated carboxylic acid, which is directly fluorinated, and then pyrolyzed to obtain a fluorinated sulfonyl fluoride having a fluoroformyl group:

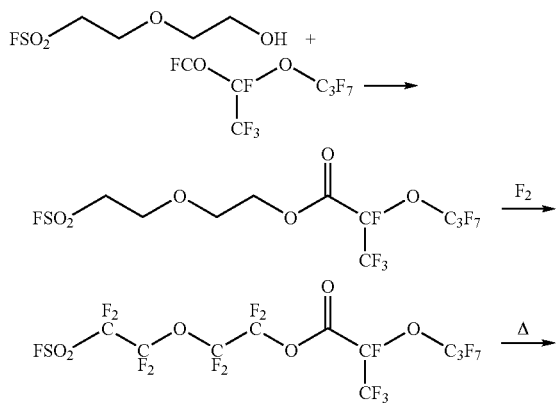

However, in this process also, since the starting material is limited to a compound derived from sulfonic acid such as isethionic acid, the skeleton of a compound to be obtained is limited.

Further, $FSO_2(CH_2)_2O(CH_2)_2OH$ to be used in the above process is known to be obtainable by a method of reacting $NaOCH_2CH_2OH$ with $FSO_2(CH_2)_2Cl$. Moreover, as another method, a method of fluorinating $ClSO_2(CH_2)_2O(CH_2)_2OH$ is also considered.

However, the former method has a problem in low yield of the product since $NaOCH_2CH_2OH$ reacts also with the $FSO_2$— group. Further, the latter method has such a problem that conditions in an oxidation step in the process for producing $ClSO_2(CH_2)_2O(CH_2)_2OH$ are disadvantageous for industrial application.

DISCLOSURE OF THE INVENTION

The present invention has been made to solve the above problems of prior art, and to provide a process for producing fluorinated sulfonyl fluorides having various molecular structures efficiently at a low cost, which solves difficulty in production.

The present inventors have found that an aimed fluorinated sulfonyl fluoride can be produced by a process which comprises reacting a sulfonyl halide compound having a specific structure with fluorine in a liquid phase and decomposing the reaction product, and accomplished the present invention.

Namely, the present invention provides the following (1) to (9)

(1) A process for producing a fluorinated sulfonyl fluoride represented by the following formula (4), which comprises oxidizing a compound represented by the following formula (1) by means of an oxidizing agent essentially containing a halogen atom to obtain a compound represented by the following formula (2), and in a case that X in the compound represented by the formula (2) is a fluorine atom, reacting the compound with fluorine in a liquid phase as it is, to obtain a compound represented by the following formula (3), and in a case that X in the compound represented by the formula (2) is a halogen atom other than a fluorine atom, converting X into a fluorine atom, and then reacting the obtained compound with fluorine in a liquid phase to obtain a compound represented by the following formula (3), and then decomposing the compound represented by the formula (3):

$$Y—S—R^A\text{-}E\text{-}R^B \tag{1}$$

$$XSO_2—R^A\text{-}E\text{-}R^B \tag{2}$$

$$FSO_2—R^{AF}\text{-}E^F\text{-}R^{BF} \tag{3}$$

$$FSO_2—R^{AF}—COF \tag{4}$$

wherein $R^A$ is a bivalent organic group;
$R^B$ is a monovalent organic group;
E is —$CH_2OCO$—, and the carbon atom constituting the keto group in E is bonded to $R^A$ or $R^B$;
Y is a hydrogen atom, a monovalent organic group or a —$SO_3M$ group (wherein M is an alkali metal atom);
X is a halogen atom;

$R^{AF}$ is the same group as $R^A$ or a bivalent organic group having $R^A$ fluorinated;

$R^{BF}$ is the same group as $R^B$ or a monovalent organic group having $R^B$ fluorinated; and $E^F$ is $-CF_2OCO-$, and the carbon atom constituting the keto group in $E^F$ is bonded to $R^{AF}$ or $R^{BF}$.

(2) The process according to (1), wherein the reaction with fluorine in a liquid phase is a perfluorination reaction.

(3) The process according to (1) or (2), wherein X is a chlorine atom.

(4) A process for producing a fluorinated vinyl compound represented by the following formula (6), which comprises adding hexafluoropropylene oxide to the compound represented by the following formula (4) obtained by the process as defined in any one of (1) to (3), to obtain a compound represented by the following formula (5), and subjecting the compound represented by the formula (5) to a decomposition reaction:

$$FSO_2-R^{AF}-COF \qquad (4)$$

$$FSO_2-R^{AF}-CF_2OCF(CF_3)COF \qquad (5)$$

$$FSO_2-R^{AF}-CF_2OCF=CF_2 \qquad (6)$$

wherein $R^{AF}$ is as defined above.

(5) A process for producing a compound represented by the following formula (4a), which comprises oxidizing a compound represented by the following formula (1a) by means of an oxidizing agent essentially containing a chlorine atom or a bromine atom to obtain a compound represented by the following formula (2a), converting the $X^ASO_2-$ group in the compound represented by the formula (2a) into a $FSO_2-$ group to obtain a compound represented by the following formula (2aF), reacting the compound represented by the formula (2aF) with fluorine in a liquid phase for perfluorination to obtain a compound represented by the following formula (3a), and further decomposing the compound represented by the formula (3a):

$$NCS-Q-CH_2OCO-R^{BF1} \qquad (1a)$$

$$X^ASO_2-Q-CH_2OCO-R^{BF1} \qquad (2a)$$

$$FSO_2-Q-CH_2OCO-R^{BF1} \qquad (2aF)$$

$$FSO_2-Q^F-CF_2OCO-R^{BF1} \qquad (3a)$$

$$FSO_2-Q^F-COF \qquad (4a)$$

wherein Q is an alkylene group, $Q^F$ is a group having Q perfluorinated and represents a perfluoroalkylene group, $X^A$ is a chlorine atom or a bromine atom, $R^{BF1}$ is a $C_{1-20}$ perfluoroalkyl group or a $C_{1-20}$ perfluoroalkyl group having an etheric oxygen atom.

(6) The process according to (5), wherein oxidation of the compound represented by the formula (1a) is carried out by reacting it with chlorine in a solvent essentially containing water to obtain a compound represented by the formula (2a) wherein $X^A$ is a chlorine atom, and the compound represented by the formula (2a) is reacted with potassium fluoride in a liquid phase to convert it into the compound represented by the formula (2aF).

(7) The process according to (5) or (6), wherein Q is a $C_{2-10}$ alkylene group, and $Q^F$ is a $C_{2-10}$ perfluoroalkylene group.

(8) The process according to any one of (S) to (7), wherein Q is a $C_{2-10}$ linear alkylene group, and $Q^F$ is a $C_{2-10}$ linear perfluoroalkylene group.

(9) A process for producing a compound represented by the following formula (6a), which comprises adding hexafluoropropylene oxide to the compound represented by the following formula (4a) obtained by the process as defined in any one of (5) to (8), to obtain a compound represented by the following formula (5a), and subjecting the compound represented by the formula (5a) to a decomposition reaction:

$$FSO_2-Q^F-COF \qquad (4a)$$

$$FSO_2-Q^F-CF_2OCF(CF_3)COF \qquad (5a)$$

$$FSO_2-Q^F-CF_2OCF=CF_2 \qquad (6a)$$

wherein $Q^F$ is as defined above.

BEST MODE FOR CARRYING OUT THE INVENTION

In this specification, the compound represented by the above formula (1) will be referred to simply as "the compound 1". The compounds of other formulae will be referred to in the same manner.

In this specification, "an organic group" means a group containing at least one carbon atom. A "saturated" group means a group wherein carbon-carbon bonds are solely single bonds.

A "halogeno group" means a group having at least one hydrogen atom bonded to a carbon atom substituted by a halogen atom. A "perhalogeno group" means a group having substantially all of hydrogen atoms bonded to carbon atoms substituted by halogen atoms. A "partially halogeno group" means a group having some of hydrogen atoms bonded to carbon atoms substituted by halogen atoms. In a case that, in a group substituted by halogen atoms, the halogen atoms are fluorine atoms, they may be referred to as "fluoro", "perfluoro", "partially fluoro", etc.

A "perfluoro group" is a group having all of hydrogen atoms bonded to carbon atoms substituted by fluorine atoms. However, even when unsubstituted hydrogen atoms remain, so long as the nature as a group is substantially equal to a "perfluoro group", such a group will be included in the concept of the "perfluoro group" in the present invention.

In the present invention, a "hetero atom-containing" group means a group containing hetero atom(s) such as oxygen atom(s), nitrogen atom(s) or sulfur atom(s), or hetero atom group(s) such as $-C-C(O)-C-$ or $-C-SO_2-C-$. The hetero atom-containing group is preferably a group containing etheric oxygen atom(s) ($-O-$).

In the present invention, the "fluorination" means to introduce fluorine atoms into a compound. The fluorination is usually a reaction to substitute hydrogen atoms bonded to carbon atoms by fluorine atoms. In a case that an unsaturated bond is contained in an organic group, addition of fluorine atoms to the unsaturated bond is also included in the fluorination.

The production process of the present invention is a production process comprising a plurality of reaction steps. In the following description, in a case that a reaction product formed by a specific reaction step is used for the subsequent step, it may be used for the subsequent reaction or the like as it is, but is preferably purified in order that a reaction in the subsequent step will smoothly proceed. As a method for purifying such a crude product, a method of distillating the crude product as it is, a method of treating the crude product with a diluted alkaline water or the like, followed by liquid separation, a method of extracting the crude product with a proper organic solvent, followed by distillation, or silica gel column chromatography may, for example, be mentioned.

The production process of the present invention is a process which comprises oxidizing a compound 1 by means of an oxidizing agent essentially containing a halogen atom to obtain a compound 2, and in a case that X in the compound 2 is a fluorine atom, reacting the compound with fluorine in a liquid phase as it is to obtain a compound 3, and in a case that X in the compound 2 is a halogen atom other than a fluorine atom, converting X into a fluorine atom, and then reacting the obtained compound with fluorine in a liquid phase to obtain a compound 3, and then decomposing the compound 3 to obtain the following compound 4:

$$Y-S-R^A-E-R^B \quad (1)$$

$$XSO_2-R^A-E-R^B \quad (2)$$

$$FSO_2-R^{AF}-E^F-R^{BF} \quad (3)$$

$$FSO_2-R^{AF}-COF \quad (4)$$

In the compound 1, $R^A$ is a bivalent organic group, and $R^B$ is a monovalent organic group. E is $-CH_2OCO-$, and the carbon atom constituting the keto group in E is bonded to $R^A$ or $R^B$. Y is a hydrogen atom, a monovalent organic group or a $-SO_3M$ group (wherein M is an alkali metal atom).

$R^A$ may be a bivalent hydrocarbon group, a halogeno bivalent hydrocarbon group, a hetero atom-containing bivalent hydrocarbon group or a halogeno(hetero atom-containing bivalent hydrocarbon) group, and it is preferably a bivalent saturated hydrocarbon group or a hetero atom-containing bivalent saturated hydrocarbon group, particularly preferably a bivalent saturated hydrocarbon group. The hetero atom-containing group is particularly preferably a group containing an etheric oxygen atom. In a case that $R^A$ is a group containing a halogen atom, it is preferably a partially halogeno group, particularly preferably a partially fluoro group. $R^A$ has preferably from 1 to 10 carbon atoms. Further, $R^A$ may have any of a linear structure, a branched structure, a cyclic structure and a structure partially having a cyclic structure, and it particularly preferably has a linear structure. $R^A$ is preferably an alkylene group, more preferably a linear alkylene group (i.e. a methylene group or a polymethylene group). $R^A$ is preferably a group (Q) as described hereinafter.

$R^B$ is preferably a monovalent organic group having fluorine atom(s). Such a monovalent organic group may be a monovalent hydrocarbon group or a hetero atom-containing monovalent hydrocarbon group, and it is preferably a monovalent saturated hydrocarbon group or a hetero atom-containing monovalent saturated hydrocarbon group. The hetero atom-containing group is particularly preferably a group containing an etheric oxygen atom. The structure of $R^B$ may be any of a linear structure, a branched structure, a cyclic structure and a structure partially having a cyclic structure, and it is preferably a linear structure or a branched structure. $R^B$ has preferably from 1 to 20, particularly preferably from 2 to 20 carbon atoms. $R^B$ is preferably a fluoroalkyl group or a fluoro(etheric oxygen atom-containing) alkyl group, and is preferably a perfluoroalkyl group or a perfluoro(etheric oxygen atom-containing) alkyl group. R may be groups as disclosed in specific examples of the compound 1, and is preferably $R^{BF1}$ as described hereinafter.

Y is a hydrogen atom, a monovalent organic group or a $-SO_3M$ group (wherein M is an alkali metal atom). In a case that Y is a monovalent organic group, it is preferably an alkoxythiocarbonyl group (a group represented by $R^aOC(=S)-$, wherein $R^a$ is an alkyl group), a dialkylaminothiocarbonyl group (a group represented by $(R^b)_2NC(=S)-$, wherein $R^b$ is an alkyl group), a cyano group, a benzyl group or a diaminomethylium group (a group represented by $-C^+(NH_2)_2Z^-$, wherein Z corresponds to Z in the formula (5) as described hereinafter, and represents a halogen atom, an alkyl sulfonyloxy group or an aryl sulfonyloxy group). Y is particularly preferably a cyano group or an alkoxythiocarbonyl group, especially preferably a cyano group.

According to the production process of the present invention, which employs a specific compound 1, the compound 4 can be produced by a process more advantageous than a conventional process. The present invention provides a process which comprises oxidizing the following compound 1a by means of an oxidizing agent essentially containing a chlorine atom or a bromine atom to obtain the following compound 2a, converting the $X^ASO_2-$ group in the compound 2a into a $FSO_2-$ group to obtain the following compound 2aF, reacting the compound 2aF with fluorine in a liquid phase to obtain the following compound 3a, and further decomposing the compound 3a to obtain the following compound 4a:

$$NCS-Q-CH_2OCO-R^{BF1} \quad (1a)$$

$$X^ASO_2-Q-CH_2OCO-R^{BF1} \quad (2a)$$

$$FSO_2-Q-CH_2OCO-R^{BF1} \quad (2aF)$$

$$FSO_2-Q-CF_2OCO-R^{BF1} \quad (3a)$$

$$FSO_2-Q^F-COF \quad (4a)$$

wherein Q, $X^A$ and $Q^F$ are as defined above. $R^{BF1}$ is a $C_{1-20}$ perfluoroalkyl group or a $C_{1-20}$ perfluoroalkyl group having an etheric oxygen atom, and is preferably such a group having from 2 to 20 carbon atoms.

The compound 1 is preferably the following compound 1a:

$$NCS-Q-CH_2OCO-R^{BF1} \quad (1a)$$

Q is an alkylene group, preferably a $C_{2-20}$ alkylene group, particularly preferably a $C_{2-10}$ linear alkylene group.

As examples of $R^{BF1}$, perfluorinated groups among specific examples of $R^{B1}$ may be mentioned.

As specific examples of the compound 1, the following compounds may be mentioned. In the following formulae, $R^{B1}$ is $-(CF_2)_aF$ (wherein a is an integer of from 1 to 20, preferably from 2 to 5), $-(CF_2)_bH$ (wherein b is an integer of from 1 to 20, preferably from 2 to 5), $-CF(CF_3)_2$, $-CF(CF_3)O(CF_2)_3F$ or $-CF(CF_3)OCF_2CF(CF_3)O(CF_2)_3F$:

$NCSCH_2CH_2CH_2OCOR^{B1}$, $NCSCH_2CH_2CH_2CH_2OCOR^{B1}$, $CH_3CH_2OC(S)SCH_2CH_2CH_2OCOR^{B1}$, $CH_3CH_2OC(S)SCH_2CH_2CH_2CH_2OCOR^{B1}$, $NCSCH_2CH_2COOCH_2R^{B1}$, $CH_3CH_2OC(S)SCH_2CH_2CH_2COOCH_2R^{B1}$.

A method for preparing the compound 1 will be described hereinafter.

In the present invention, the compound 1 is oxidized by means of an oxidizing agent essentially containing a halogen atom to obtain the compound 2. In the compound 2, $R^A$, $R^B$ and E are as defined for the formula (1). X is a halogen atom. X is preferably a chlorine atom. That is, in the present invention, it is preferred that a compound 2 wherein X is a chlorine atom is obtained, the chlorine atom in the compound 2 is substituted by a fluorine atom by a method as described hereinafter, and then the obtained compound is fluorinated in a liquid phase.

The compound 2 to be directly formed by the reaction with an oxidizing agent is preferably the following compound 2a (wherein Q and $R^{BF1}$ are as defined above, and their preferred embodiments are also the same, and $X^A$ is a chlorine atom or a bromine atom):

$$X^A SO_2\text{-}Q\text{-}CH_2OCO\text{—}R^{BF1} \quad (2a)$$

The compound 2 to be formed by the oxidation reaction of the compound 1 is a compound wherein the Y—S— group in the compound 1 is converted into a X—$SO_2$— group. The method of the oxidation reaction may optionally be changed depending upon the type of X in the compound 2.

For example, as a method to form a compound 2 wherein X is a halogen atom other than a fluorine atom (hereinafter such a halogen atom will be referred to as another halogen atom and represented by $X^1$) by the oxidation reaction of the compound 1, a method of reacting the compound 1 with another halogen (($X^1$)$_2$) in a solvent essentially containing water may be mentioned. Such a method is a method particularly preferred when Y in the compound 1 is a $R^aOC(=S)$— group (wherein $R^a$ is as defined above), a cyano group or a benzyl group.

For example, a method to form a compound 2 wherein X is a chlorine atom is preferably a method of reacting the compound 1 with chlorine ($Cl_2$) in a solvent essentially containing water. Further, in a case of forming a compound 2 wherein X is a bromine atom, preferred is a method of reacting the compound 1 with bromine ($Br_2$) in a solvent essentially containing water. Such methods can be carried out in accordance with known means (New Experimental Chemistry, The Chemical Society of Japan, Maruzen Company, Limited, Tokyo, 1978, vol. 14, Syntheses and reactions of organic compounds (III), pages 1,785 to 1,786, etc.).

In a case of carrying out a reaction with chlorine, a method of employing chlorine gas or a method of employing chlorine gas diluted with an inert gas may be mentioned. The inert gas is preferably nitrogen gas or helium gas, particularly preferably nitrogen gas. In a case of employing an inert gas, the amount of the chlorine gas based on the total amount of the inert gas and the chlorine gas is preferably at least 10 vol % from the viewpoint of efficiency, particularly preferably at least 20 vol %.

The solvent essentially containing water is preferably water, a mixed solvent of water with acetic acid or a mixed solvent of water with acetonitrile. The amount of such a solvent is preferably at least two times by mass, particularly preferably from 5 to 50 times by mass, to the compound 1. The amount of water is preferably from 4 to 2,000 times by mol, particularly preferably from 20 to 1,000 times by mol, to the compound 1.

The reaction temperature in the reaction of the compound 1 with another halogen (($X^1$)$_2$) is usually preferably at least $-20°$ C., and preferably from $0°$ C. to $+60°$ C. from the viewpoint of the reaction yield, the selectivity and the efficiency for industrial operation. The reaction pressure in the chlorination reaction is preferably from normal pressure to 2 MPa from the viewpoint of the reaction yield, the selectivity and the efficiency for industrial operation. The reaction with another halogen (($X^1$)$_2$) is considered to proceed in such a manner that another halogen (($X^1$)$_2$) reacts with water to form $HX^1O$, and this $HX^1O$ oxidizes the sulfur atom and simultaneously, the Y—S bond undergoes oxidative cleavage.

On the other hand, in a case of forming a compound 1 wherein X is a fluorine atom by the oxidation reaction of the compound 1, preferred is a method of reacting the compound 1, hydrofluoric acid and nitrogen dioxide.

Among specific examples of the compound 2, as examples wherein X is a chlorine atom, the following compounds may be mentioned. In the following formulae, $R^{B1}$ is as defined above. As specific examples of a compound 2 wherein X is a bromine atom or a fluorine atom, examples wherein Cl in the following compounds is changed to Br or F may be mentioned:

$ClSO_2CH_2CH_2CH_2OCOR^{B1}$, $ClSO_2CH_2CH_2CH_2CH_2OCOR^{B1}$, $ClSO_2CH_2CH_2COOCH_2R^{B1}$.

In the present invention, the compound 2 to be reacted with fluorine in the subsequent step is the following compound 2F wherein X is a fluorine atom. In a case of a compound 2 wherein X is another halogen atom, X is converted into a fluorine atom to convert the compound 2 into the compound 2F, and the obtained compound 2F is fluorinated, whereby such an advantage can be obtained that the yield in the fluorination reaction remarkably improves:

$$FSO_2\text{—}R^A\text{-}E\text{-}R^B \quad (2F)$$

The compound 2F is preferably the following compound 2aF wherein $X^A$ in the compound 2a is substituted by a fluorine atom (wherein Q and $R^{BF1}$ are as defined above, and their preferred embodiments are also the same):

$$FSO_2\text{-}Q\text{-}CH_2OCO\text{—}R^{BF1} \quad (2aF)$$

In a case that X in the compound 2 is another halogen atom, a known method may be employed as a method of substituting another halogen atom by a fluorine atom. For example, in a case that X in the compound 2 is a chlorine atom, as a substitution reaction of substituting the chlorine atom by a fluorine atom, a method of reacting the compound 2 with potassium fluoride (Scott, R. B.; Gordon M. J., J. Org. CHem. 1956, 21, 385.) or with potassium hydrogen fluoride (Gramstad, T.; Hazeldine, R. N. J. CHem. Soc. 1956, 173.), in a liquid phase, may be mentioned.

Such a substitution reaction is carried out preferably in the presence of a solvent. The solvent is preferably a mixed solvent of water with dioxane or a mixed solvent of water with acetonitrile. The amount of the solvent is preferably at least two times by mass, particularly preferably from 5 to 50 times by mass, to the compound 2F.

The reaction temperature in the substitution reaction is usually preferably from $-20°$ C. to the boiling point of the solvent, and preferably from $0°$ C. to $+60°$ C. from the viewpoint of the reaction yield, the selectivity and the efficiency for industrial operation. The reaction pressure in the substitution reaction is not particularly limited, and it is particularly preferably from normal pressure to 2 MPa from the viewpoint of the reaction yield, the selectivity and the efficiency for industrial operation.

As specific examples of the compound 2F wherein X is a fluorine atom, compounds wherein Cl bonded to $SO_2$ in the above specific examples of the compound 2 is substituted by F may be mentioned.

In the present invention, the compound 2F is reacted with fluorine in a liquid phase for fluorination to obtain the compound 3.

The fluorination reaction in the fluorination step is carried out by a liquid phase fluorination reaction carried out in a liquid phase from the viewpoint of the yield and the operation efficiency of the reaction (Okazoe T. et al., Adv. Synth. Catal., 2001, 343, 219.). Such a fluorination reaction may be carried out theoretically by an ECF method, a cobalt fluorination method or a method of reaction with fluorine in a gas phase. However, from the viewpoint of the reaction yield, the efficiency in the reaction operation, etc., fluorination in a liquid phase is a remarkably advantageous method. The fluorination reaction in a liquid phase is preferably carried out by a method wherein the compound 2F is reacted with fluorine ($F_2$) in the presence of a solvent to form the compound 3.

In the present invention, the fluorine content of the compound 2F is preferably at least 30 mass %. When the fluorine content is at least 30 mass %, favorable solubility in a liquid phase will be achieved at the time of the fluorination reaction. The fluorine content of the compound 2F may be suitably adjusted depending upon the type of the liquid phase for the fluorination reaction. However, the fluorine content is more preferably from 30 to 86 mass %, furthermore preferably from 30 to 76 mass %. Use of the compound 2F having a fluorine content of at most 86 mass % is advantageous from the viewpoint of economical efficiency and unlimited available compounds.

Further, the molecular weight of the compound 2F is preferably from 200 to 1,300. When the molecular weight of the compound 2F is at least 200, a decrease in boiling point of the compound 2F will be suppressed, and the compound 2F will be prevented from volatilizing to decrease the yield of the fluorinated product or to lead a decomposition reaction in the process of the fluorination. On the other hand, when the molecular weight is at most 1,300, a decrease in solubility in a liquid phase will be suppressed.

As the fluorine, fluorine gas may be employed as it is, or fluorine gas diluted with an inert gas may be employed. As such an inert gas, nitrogen gas or helium gas is preferred, and from the economical reason, nitrogen gas is particularly preferred. The amount of fluorine in nitrogen gas is not particularly limited, it is preferably at least 10 vol % from the viewpoint of the efficiency, particularly preferably at least 20 vol %.

The solvent for fluorination is preferably a solvent containing no C—H bond and essentially containing C—F bond(s) More preferred is a perfluoroalkane or an organic solvent obtained by perfluorinating a known organic solvent having in its structure at least one atom selected from the group consisting of a chlorine atom, a nitrogen atom and an oxygen atom. Further, as such a solvent, it is preferred to employ a solvent in which the solubility of the compound 2F is high, and it is particularly preferred to employ a solvent which is capable of dissolving at least 1 mass % of the compound 2F, especially preferred to employ a solvent capable of dissolving at least 5 mass % of the compound 2F.

Examples of the solvent include solvents as disclosed in the fluorination step in WO02/44138. The amount of the solvent to the compound 2F is preferably at least five times by mass, particularly preferably from 10 to 100 times by mass.

The reaction system for the fluorination reaction may be a batch system or a continuous system. Methods as disclosed in WO02/44138 will be applicable to the respective methods. The fluorine gas may be one diluted with an inert gas such as a nitrogen gas in either case where the reaction is carried out in a batch system or in a continuous system.

With respect to the amount of fluorine to be used for the fluorination reaction, in either case where the reaction is carried out by a batch system or a continuous system, it is preferably such that the amount of fluorine is always in excess equivalent to hydrogen atoms to be fluorinated, and it is particularly preferably such that it would be at least 1.5 times by mol from the viewpoint of the selectivity. Further, the amount of fluorine gas is preferably maintained in an excess amount always from the initiation to the termination of the reaction.

The reaction temperature for the fluorination reaction is usually preferably from −60° C. to the boiling point of the compound 2F, and from the viewpoint of the reaction yield, the selectivity and the efficiency for industrial operation, it is particularly preferably from −50° C. to +100° C., especially preferably from −20° C. to +50° C. The reaction pressure for the fluorination reaction is not particularly limited, and from the viewpoint of the reaction yield, the selectivity and the efficiency for industrial operation, it is particularly preferably from normal pressure to 2 MPa.

Further, in order to let the fluorination reaction proceed efficiently, it is preferred to add a C—H bond-containing compound to the reaction system at a later stage of the reaction or to carry out ultraviolet irradiation. As the addition method, the addition amount and specific compounds, specific examples as disclosed in the fluorination step in WO02/44138 will be applicable.

$R^{AF}$ in the compound 3 is a group having $R^A$ fluorinated, and in a case that $R^A$ is a group incapable of being fluorinated or in a case that $R^A$ is a group capable of being fluorinated but is not fluorinated, $R^{AF}$ is the same group as $R^A$. For example, in a case that $R^A$ is a perfluoro group, it would not change even when reacted with fluorine in a liquid phase, and accordingly, $R^{AF}$ is the same group as $R^A$. $R^A$ is preferably a group capable of being fluorinated, and $R^{AF}$ is more preferably a group having $R^A$ fluorinated, particularly preferably a perfluorinated group. $R^{BF}$ is a group having $R^B$ fluorinated, and in a case that $R^B$ is a group incapable of being fluorinated or in a case that $R^B$ is a group capable of being fluorinated but is not fluorinated, $R^{BF}$ is the same group as $R^B$. $R^B$ is preferably the same perfluorinated monovalent organic group as $R^{BF}$.

The fluorination reaction in the present invention is preferably a reaction of perfluorinating the compound 2F, and the compound 3 is preferably a compound having the compound 2F perfluorinated.

Namely, in the compound 3, $R^{AF}$ is preferably a perfluorinated bivalent organic group, particularly preferably a perfluoro bivalent saturated hydrocarbon group or a perfluoro (hetero atom-containing bivalent saturated hydrocarbon) group, especially preferably a perfluoro bivalent saturated hydrocarbon group. $R^{BF}$ is preferably a perfluorinated group, and preferably a perfluoro monovalent saturated hydrocarbon group or a perfluoro(hetero atom-containing monovalent saturated hydrocarbon) group.

$E^F$ in the compound 3 is —CF$_2$OCO—, and the carbon atom constituting the keto group is bonded to $R^{AF}$ or $R^{BF}$. The direction of —CF$_2$OCO— is the same direction corresponding to the direction of E in the compound 2, and in a case that the keto group in —CH$_2$OCO— in E is boned to $R^A$, the keto group in —CF$_2$OCO— in $E^F$ is bonded to $R^{AF}$. On the other hand, in a case that the keto group in E is bonded to $R^B$, the keto group in $E^F$ is bonded to $R^{BF}$.

The compound 3 is preferably the following compound 3a obtained by fluorinating the compound 2a. In the following formula, $R^{BF1}$ is as defined above, and its preferred embodiment is also the same:

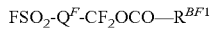  (3a)

$Q^F$ is a group having Q perfluorinated and represents a perfluoroalkylene group. $Q^F$ is preferably a $C_{2-10}$ perfluoroalkylene group, particularly preferably a $C_{2-10}$ linear perfluoroalkylene group.

As specific examples of the compound 3, the following compounds may be mentioned. In the following formulae, $R^{BF1}$ is —$(CF_2)_aF$ (wherein a is an integer of from 1 to 20 and is preferably from 2 to 5), —$CF(CF_3)_2$, —$CF(CF_3)OCF_2CF_2CF_3$, or —$CF(CF_3)OCF_2CF(CF_3)OCF_2CF_2CF_3$:

$FSO_2(CF_2)_3OCOR^{BF1}$, $FSO_2(CF_2)_4OCOR^{BF1}$, $FSO_2(CF_2)_2COOR^{BF1}$.

In the present invention, the compound 3 is decomposed to obtain the compound 4. To the decomposition step, a means of reaction known as a decomposition reaction of the ester bond will be applicable, and this step is carried out preferably by a pyrolytic reaction or by a decomposition reaction which is carried out in the presence of a nucleophilic agent or an electrophilic agent (Okazoe T. et al., Adv. Synth. Catal. 2001, 343, 219. ).

The pyrolytic reaction can be carried out by heating the compound 3. The reaction system for the pyrolytic reaction is preferably selected depending upon the boiling point and stability of the compound 3. For example, in a case that a readily vaporizable compound 3 is to be pyrolyzed, it is possible to employ a gas phase pyrolytic method wherein the pyrolysis is continuously carried out in a gas phase, and a discharge gas containing the obtained compound 4 is condensed and recovered.

The reaction temperature in the gas phase pyrolytic method is preferably from 50 to 350° C., particularly preferably from 50 to 300° C., especially preferably from 150 to 250° C. Further, an inert gas which is not directly involved in the reaction, may also be present in the reaction system. As such an inert gas, nitrogen gas or carbon dioxide gas may, for example, be mentioned. Such an inert gas is preferably added in an amount of from about 0.01 to about 50 vol %, based on the compound 3. If the amount of the added inert gas is large, the yield of the product may sometimes be reduced.

On the other hand, in a case that the compound 3 is a hardly vaporizable compound, it is preferred to employ a liquid phase pyrolytic method wherein it is heated in the state of a liquid in a reactor. The pressure for the reaction in this case is not particularly limited. In a usual case, the product containing the compound 4 has a lower boiling point, and therefore, it is preferred to obtain it by a method of a reaction distillation system wherein the product is vaporized and continuously withdrawn. Otherwise, a method may be employed wherein after completion of the heating, the product is withdrawn all at once from the reactor. The reaction temperature in such a liquid phase pyrolytic method is preferably from 50 to 300° C., particularly preferably from 100 to 250° C.

In a case that pyrolysis is carried out by the liquid phase pyrolytic method, it may be carried out in the absence of any solvent or in the presence of a solvent. The solvent is not particularly limited, so long as it is one which is not reactive with the compound 3 and is soluble in each other with the compound 3 and which is not reactive with the compound 4 to be formed. Further, as the solvent, it is preferred to select one which can readily be separated at the time of purification of the compound 4. Specific examples of the solvent 6 include inert solvents such as a perfluorotrialkylamine and a perfluoronaphthalene, and a chlorotrifluoroethylene oligomer (for example, tradename: FLON LUBE) having a high boiling point among chlorofluorocarbons, are preferred. The amount of the solvent is preferably from 10 to 1,000 mass %, based on the compound 3.

Further, in a case that the compound 3 is reacted with a nucleophilic agent or an electrophilic agent in a liquid phase for decomposition, such a reaction may be carried out in the absence of any solvent or in the presence of a solvent. As the solvent, the same solvents explained as the solvents for the liquid phase pyrolysis are mentioned. The nucleophilic agent is preferably $F^-$, particularly preferably $F^-$ derived from an alkali metal fluoride. The alkali metal fluoride is preferably NaF, $NaHF_2$, KF or CsF. Among them, NaF or KF is particularly preferred from the viewpoint of the economical efficiency and the reactivity.

In a case that a nucleophilic agent (such as $F^-$) is employed, the nucleophilic agent to be used at the initial stage of the reaction may be in a catalytic amount or in an excess amount. The amount of the nucleophilic agent such as $F^-$ is preferably from 1 to 500 mol %, particularly preferably from 1 to 100 mol %, especially preferably from 5 to 50 mol %, based on the compound 3.

The reaction temperature is preferably from −30° C. to the boiling point of the solvent or the compound 3, particularly preferably from −20° C. to 250° C. This method is also preferably carried out in a reactor equipped with a distillation column.

The compound 4 to be obtained in the decomposition step is preferably the following compound 4a formed by the decomposition reaction of the compound 3a (in the following formula, $Q^F$ is as defined above, and its preferred embodiment is also the same):

$$FSO_2\text{-}Q^F\text{-}COF \quad (4a)$$

As specific examples of the compound 4, the following compounds may be mentioned:

$FSO_2CF_2CF_2COF$, $FSO_2CF_2CF_2CF_2COF$.

The compound 4 to be obtained by the production process of the present invention, which has a $FSO_2$— group in its terminal, is a compound useful as a starting material of a monomer for a ion-exchange resin. For derivation to such a monomer, various methods employing reactivity of the —COF group will be applicable.

As a method to prepare the compound 1 as a material in the production process of the present invention, the following Preparation Process 1 or Preparation Process 2 is preferred since compounds 1 with various structures depending upon the purpose of use will be obtained. In the following formulae, $R^A$, $R^B$, E and Y are as defined above, one of $E^1$ and $E^2$ is —$CH_2OH$, and the other is —COW (wherein W is a halogen atom or a hydroxyl group), and Z is a halogen atom, an alkyl sulfonyloxy group or an aryl sulfonyloxy group.

Preparation Process 1

A process of subjecting a compound 5 and a compound 6 to an esterification reaction to obtain a compound 7, and then reacting the compound 7 with a sulfur nucleophile to obtain the compound 1.

$$Z\text{—}R^A\text{-}E^1 \quad (5)$$

$$R^B\text{-}E^2 \quad (6)$$

$$Z\text{—}R^A\text{-}E\text{-}R^B \quad (7)$$

$$Y\text{—}S\text{—}R^A\text{-}E\text{-}R^B \quad (1)$$

In a case that Z is a halogen atom, it is preferably a chlorine atom or a bromine atom. In a case that Z is an alkyl sulfonyloxy group, the alkyl moiety in the group is preferably a $C_{1-6}$ alkyl group. In a case that Z is an aryl sulfonyloxy group, the aryl moiety in the group is preferably a $C_{6-10}$ aryl group. Further, the alkyl moiety or the aryl moiety in Z may optionally be substituted. Z is particularly preferably a chlorine atom, a bromine atom, a methane sulfonyloxy group, a trifluoromethane sulfonyloxy group, a benzene sulfonyloxy group or a toluene sulfonyloxy group.

One of $E^1$ and $E^2$ is —$CH_2OH$, and the other is —COW (wherein W is a halogen atom or a hydroxyl group). It is preferred that $E^1$ is —$CH_2OH$ and $E^2$ is —COW. W is preferably a fluorine atom, a chlorine atom or a hydroxyl group.

The esterification reaction of the compound 5 and the compound 6 may be carried out under conditions for known esterification reactions. In the esterification reaction, E(—$CH_2OCO$—) forms by the reaction of $E^1$ with $E^2$.

The esterification reaction may be carried out in the presence of a solvent, but it is carried out preferably in the absence of a solvent from the viewpoint of the volume efficiency (for example, "New Experimental Chemistry", The Chemical Society of Japan, fourth edition, Vol. 22 (Organic Systheses (IV), Acids, Amino Acids and Peptides), Maruzen Company, Limited, Tokyo, 1992, pages 50 to 51). When a solvent is employed, it is preferably dichloromethane, chloroform, pyridine or diethyl ether. The amount of the solvent to be used is preferably from 50 to 500 mass % based on the total amount of the compound 5 and the compound 6.

In the esterification reaction, in a case that W is a halogen atom, an acid represented by HW forms. In a case that the substrate or the product in the reaction is a compound which is unstable against an acid, it is preferred to use a scavenger (such as a trialkylamine). Further, in a case that no scavenger is used, it is preferred to let such an acid accompany a nitrogen stream and be discharged out of the reaction system.

Further, in a case that W is a hydroxyl group, water will form, and accordingly a dehydrating agent may be made to be present in the reaction system to accelerate the progress of the reaction (for example, "New Experimental Chemistry", The Chemical Society of Japan, forth edition, Vol. 22 (Organic Synsheses (IV), Acids, Amino Acids and Peptides), Maruzen Company, Limited, Tokyo, 1992, pages 45 to 46). The dehydrating agent is preferably trifluoroacetic anhydride or thionyl chloride. The amount of the dehydrating agent to the compound 5 is preferably from 1 to 10 times by mol.

The reaction temperature for the esterification reaction is preferably from $-50°$ C. to $+100°$ C. or to the boiling temperature of the solvent. Further, the reaction time for the reaction may suitably be changed depending upon the supply rate of the compounds and the amounts of the compounds to be used for the reaction. The pressure for the reaction (the gage pressure, the same applies hereinafter) is preferably from normal pressure to 2 MPa.

A crude product formed by the esterification reaction is preferably purified by the above method.

The compound 7 formed by the esterification reaction is then reacted with a sulfur nucleophile to obtain the compound 1. The compound 1 is a compound wherein the Z moiety in the compound 7 is converted into a Y—S-moiety. Y is a hydrogen atom, a monovalent organic group or a —$SO_3M$ group (wherein M is an alkali metal atom), and the structure of the Y—S-moiety corresponds to the type of the sulfur nucleophile to be used for the reaction. In a case that Y is a monovalent organic group, it is preferably a $R^aOC(=S)$— group (wherein $R^a$ is an alkyl group), a $(R^b)_2NC(=S)$— group (wherein $R^b$ is an alkyl group), a cyano group, a benzyl group or a —$C^+(NH_2)_2Z^-$ group (wherein Z corresponds to Z in the formula (7) and represents a halogen atom, an alkyl sulfonyloxy group or an aryl sulfonyloxy group).

The sulfur nucleophile to obtain a compound 1 wherein Y is a hydrogen atom, is preferably a metal sulfide (such as a compound represented by the formula $M^1SH$, wherein $M^1$ is an alkali metal atom).

The sulfur nucleophile to obtain a compound 1 wherein Y is a monovalent organic group, may suitably be changed depending upon the type of the monovalent organic group (Y).

For example, as an example to obtain a compound 7 wherein Y is a $R^aOC(=S)$— group (wherein $R^a$ is an alkyl group), preferred is an O-alkyldithiocarbonate (such as a compound represented by the formula $R^aOC(=S)SM^2$, wherein $R^a$ is as defined above, and $M^2$ is an alkali metal atom). As an example to obtain a compound 1 wherein Y is a $(R^b)_2NC(=S)$— group (wherein $R^b$ is an alkyl group), preferred is a N,N-dialkyldithiocarbamate (such as a compound represented by $(R^b)_2NC(=S)SM^3$, wherein $R^b$ is as defined above, and $M^3$ is an alkali metal atom). As an example to obtain a compound 1 wherein Y is a cyano group, preferred is a thiocyanate (such as a compound represented by $M^4SCN$, wherein $M^4$ is an alkali metal atom). As an example to obtain a compound 1 wherein Y is a benzyl group, preferred is benzyl mercaptan ($C_6H_5CH_2SH$). As an example to obtain a compound 1 wherein Y is —$C^+(NH_2)_2Z^-$ group (wherein Z corresponds to Z in the formula (6), and Z is as defined above), preferred is thiourea (such as a compound represented by $H_2NC(=S)NH_2$).

As the sulfur nucleophile to obtain a compound 1 wherein Y is —$SO_3M$ (wherein M is an alkali metal atom), preferred is a thiosulfate (such as a compound represented by the formula MO—SO(=S)—OM, wherein M is as defined above).

Among them, the sulfur nucleophilic agent is particularly preferably an O-alkyldithiocarbonate, a thiocyanate or a benzyl mercaptan, and Y corresponding to the sulfur nucleophilic agent is preferably a $R^aOC(=S)$—group (wherein $R^a$ is as defined above), a cyano group or a benzyl group. The reaction with the sulfur nucleophilic agent may be carried out in accordance with a known method (New Experimental Chemistry (The Chemical Society of Japan), Maruzen Company, Limited, Tokyo, 1978, Vol. 14, pages 1,701 to 1,706).

The reaction with the sulfur nucleophile is carried out preferably in the presence of a solvent. The solvent is preferably water, ethanol, acetone or N,N-dimethylformamide. The amount of the solvent to be used is preferably from 50 to 500 mass % based on the total amount of the compound 7 and the sulfur nucleophile.

The temperature for the reaction of the compound 7 with the sulfur nucleophile is preferably from $0°$ C. to $+100°$ C. or to the boiling temperature of the solvent. Further, the reaction time for the reaction may suitably be changed depending upon the supply rate of the materials and the amounts of the compounds to be used for the reaction. The pressure for the reaction is preferably from normal pressure to 2 MPa.

Preparation Process 2

A process of subjecting a compound 8 and the compound 6 to an esterification reaction to obtain the compound 1.

$$Y-S-R^A-E^1 \tag{8}$$

$$R^B-E^2 \tag{6}$$

$$Y-S-R^A-E-R^B \tag{1}$$

In the compound 8 and the compound 6, Y, $E^1$ and $E^2$ are the same groups as those groups in the Preparation Process 1, and their preferred embodiments are also the same. Further, one of $E^1$ and $E^2$ is —COW (wherein W is as defined above) and the other is —$CH_2OH$, and in a case that E is —$CH_2OCO$—, the reaction of the compound 8 with the compound 6 is an esterification reaction. This reaction can be carried out in the same manner as in the esterification reaction of the compound 5 with the compound 6 in the Preparation Process 1.

The compound 5 is preferably the following compound 5a to be formed by the decomposition reaction of the compound 4a (in the following formula, Z and Q are as defined above, and their preferred embodiments are also the same):

$$Z-Q-CH_2OH \tag{5a}$$

As specific examples of the compound 5, the following compounds may be mentioned:

BrCH$_2$CH$_2$CH$_2$OH,

BrCH$_2$CH$_2$CH$_2$CH$_2$OH,

ClCH$_2$CH$_2$CH$_2$OH,

ClCH$_2$CH$_2$CH$_2$CH$_2$OH,

BrCH$_2$CH$_2$COOH,

ClCH$_2$CH$_2$COOH,

BrCH$_2$CH$_2$COCl,

ClCH$_2$CH$_2$COCl.

Further, as specific examples of the compound 6, the following compound may be mentioned. In the following compounds, $R^{B1}$ is as defined above:

B$^{B1}$COF,

B$^{B1}$CH$_2$OH.

The compound 7 is preferably the following compound 7a (in the following formula, Z, Q and $R^{BF1}$ are as defined above, and their preferred embodiments are also the same):

Z-Q-CH$_2$OCO—R$^{BF1}$ (7a)

As specific examples of the compound 7, the following compounds may be mentioned:

BrCH$_2$CH$_2$CH$_2$OCOR$^{B1}$,

BrCH$_2$CH$_2$CH$_2$CH$_2$OCOR$^{B1}$,

ClCH$_2$CH$_2$CH$_2$OCOR$^{B1}$,

ClCH$_2$CH$_2$CH$_2$CH$_2$OCOR$^{B1}$,

BrCH$_2$CH$_2$COOCH$_2$R$^{B1}$,

ClCH$_2$CH$_2$COOCH$_2$R$^{B1}$.

As specific examples of the compound 8, the following compounds may be mentioned:

NCSCH$_2$CH$_2$CH$_2$OH,

NCSCH$_2$CH$_2$CH$_2$CH$_2$OH,

NCSCH$_2$CH$_2$COOH,

NCSCH$_2$CH$_2$COCl.

The production process of the present invention can be improved into a more efficient process by contriving the structure of compounds in the process. For example, the following Process 1 may be mentioned.

Process 1

A process to recycle a by-product in the product, and a process of employing as the compound 6 in the Preparation Process 1 the following compound 9a or the following compound 9b. In the formulae, $R^{BF}$ is as defined above:

R$^{BF}$—COF (9a)

R$^{BF}$—CH$_2$OH (9b)

The compound 9a can be obtained by the decomposition reaction of the compound 3.

The compound 9b can be obtained by a reduction reaction of the compound 9a. For example, the reduction reaction of the compound 9a is carried out preferably by a method of converting the compound 9a into a proper ester and then reacting the ester with a metal hydride in a liquid phase (for example, Niederpruem H., Voss P. Ger. 1,300,539, 3 to 4) or a method of bringing the compound 9a into contact with hydrogen gas in the presence of a proper catalyst (Novotny M., U.S. Pat. No. 4,273,947, 7 to 10).

In the reduction reaction employing a metal hydride, the metal hydride is preferably sodium borohydride or lithium aluminum hydride. It is preferred to employ tetrahydrofuran or dioxane as a solvent for the reaction. In a case that sodium borohydride is used as the metal hydride, it is also possible to employ as a solvent methanol, ethanol or 2-propanol. The amount of the solvent to the compound 9a is preferably at least two times by mass, particularly preferably from 5 to 50 times by mass.

In a case that the metal hydride is used, the reaction temperature is usually preferably from −50° C. to the boiling point of the solvent, and it is preferably from 0° C. to the boiling point of the solvent, from the viewpoint of the reaction yield, the selectivity and the efficiency for industrial operation. The reaction pressure is not particularly limited, and it is particularly preferably from normal pressure to 2 MPa from the viewpoint of the reaction yield, the selectivity and the efficiency for industrial operation.

In the method of reducing the compound 9a by bringing it into contact with hydrogen gas in the presence of a catalyst to obtain the compound 9b, the catalyst is preferably a palladium, rhodium or iridium catalyst. The reaction may be carried out in the presence of a solvent, but it is carried out preferably in the absence of a solvent from the viewpoint of the volume efficiency. The reaction temperature is usually preferably from 0 to 200° C. The reaction pressure is not particularly limited, and it is particularly preferably from normal pressure to 10 MPa from the viewpoint of the reaction yield, the selectivity and the efficiency for industrial operation.

The Process 1 can be conceptually represented by the following scheme. In the following scheme, the symbols are as defined above:

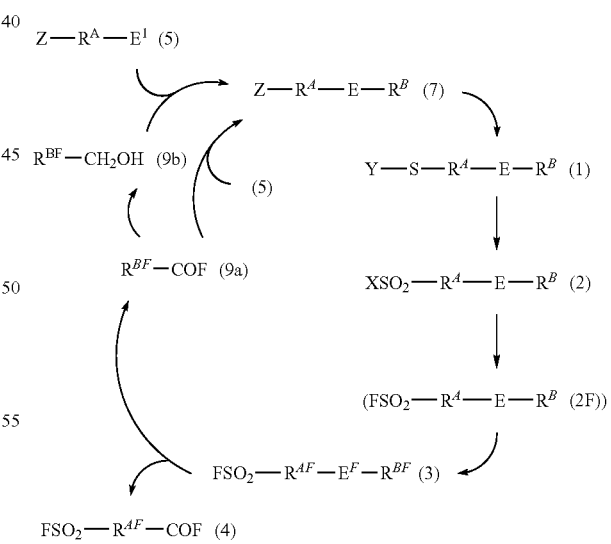

Among the Processes 1, the following Production Process 1A wherein the compound 1a is used as the starting material is particularly preferred as a process to obtain a compound 4 wherein $R^{AF}$ is a perfluoroalkylene group among the compounds 1 which are less easily produced by a conventional production process. In the following scheme, the symbols are as defined above.

Process 1A

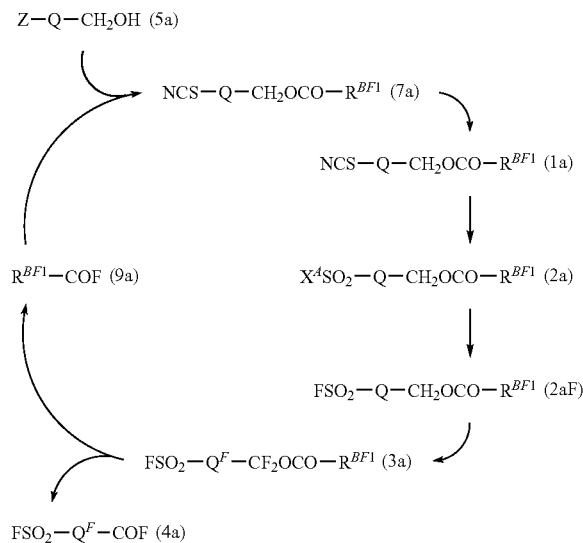

As specific examples of the Process 1, the following processes may be mentioned.

Process 1-1

The following compound 5-1 and the following compound 9a-1 are subjected to an esterification reaction to form the following compound 7-1, the compound 7-1 is reacted with a thiocyanate to form the following compound 1-1, the compound 1-1 is oxidized by reacting it with chlorine in a medium essentially containing water to obtain the following compound 2-1, and the chlorine atom bonded to $SO_2$ in the compound 2-1 is substituted by a fluorine atom to form the following compound 2-1F. Then, the compound 2-1F is reacted with fluorine in a liquid phase to form the following compound 3-1, and the compound 3-1 is decomposed to obtain the following compound 4-1 and at the same time to obtain the following compound 9a-1. The compound 9a-1 is reacted with the following compound 5-1 again. In the following scheme, $R^{BF1}$ is as defined above:

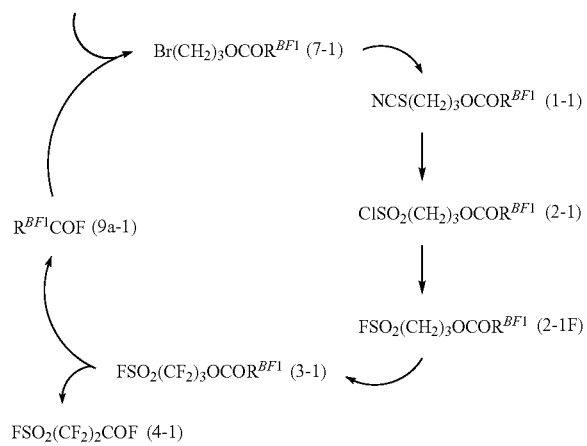

Process 1-2

The following compound 5-2 and the following compound 9a-2 are reacted to form the following compound 7-2, the compound 7-2 is reacted with a thiocyanate to form the following compound 1-2, the compound 1-2 is oxidized by reacting it with chlorine in a medium essentially containing water to obtain the following compound 2-2, and the chlorine atom bonded to $SO_2$ in the compound 2-2 is substituted by a fluorine atom to form the following compound 2-2F. Then, the compound 2-2F is reacted with fluorine in a liquid phase to form the following compound 3-2, and the compound 3-2 is decomposed to obtain the following aimed compound 4-2 and at the same time to obtain the following compound 9a-2. The compound 9a-2 is reacted with the following compound 5-2 again, and the same reactions are carried out:

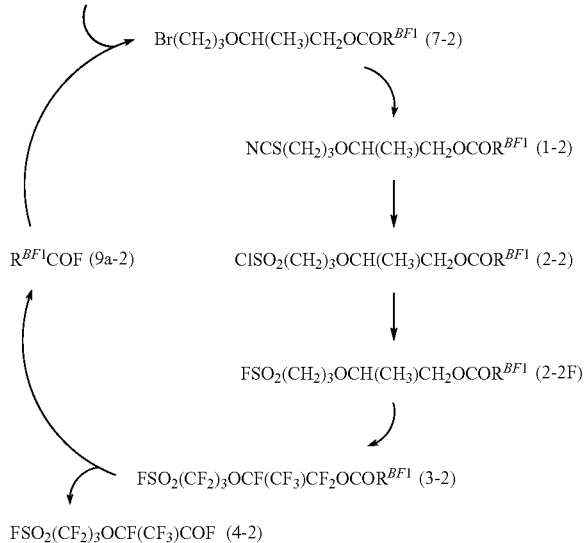

Process 1-3

The following compound 5-3 and the following compound 9b-1 are reacted to obtain the following compound 7-3, and the compound 7-3 is reacted with a thiocyanate to form the following compound 1-3. Then, the compound 1-3 is oxidized by reacting it with chlorine in a medium essentially containing water to obtain the following compound 2-3, and the chlorine atom bonded to $SO_2$ in the compound 2-3 is substituted by a fluorine atom to form the following compound 2-3F. Then, the compound 2-3F is reacted with fluorine in a liquid phase to form the following compound 3-3, and the compound 3-3 is decomposed to obtain the following compound 4-1 and at the same time to obtain the following compound 9a-1, and the compound 9a-1 is reduced to obtain the following compound 9b-1. The compound 9b-1 is reacted with the compound 5-3 again, and the same reactions are carried out:

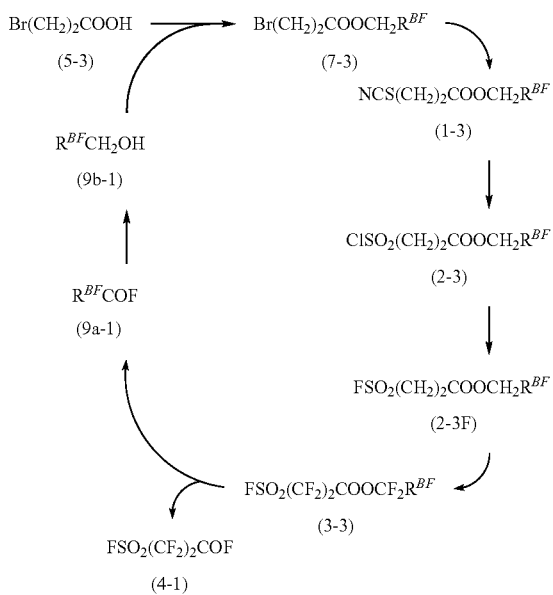

Process 1-4

The following compound 5-4 and the following compound 9b-1 are reacted to form the following compound 7-4, and the compound 7-4 is reacted with a thiocyanate to form the following compound 1-4. Then, the compound 1-4 is oxidized by reacting it with chlorine in a medium essentially containing water to obtain the following compound 2-4, and the chlorine atom bonded to $SO_2$ in the compound 2-4 is substituted by a fluorine atom to form the following compound 2-4F. Then, the compound 2-4F is reacted with fluorine in a liquid phase to form the following compound 3-4, and the compound 3-4 is decomposed to obtain the following aimed compound 4-2 and at the same time to obtain the following compound 9a-1. The compound 9a-1 is reduced to form the following compound 9b-1, and the compound 9b-1 is reacted with the following compound 5-4 again, and the same reactions are carried out:

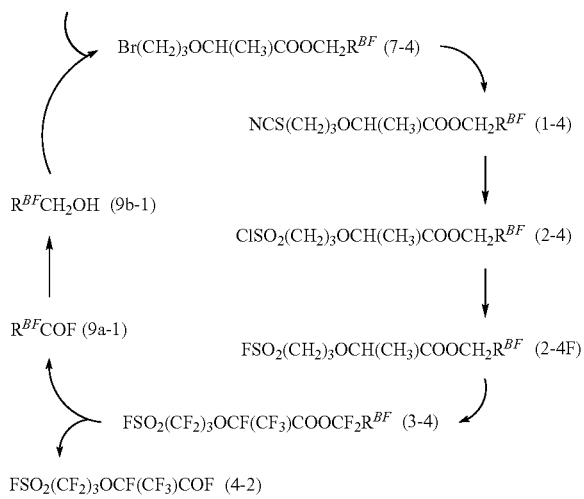

The terminal —COF group in the compound 4 produced by the process of the present invention can be converted into a —$CF_2OCF(CF_3)COF$ group by reaction with hexafluoropropylene oxide (HFPO). That is, the present invention provides a process for producing the following compound 6, which comprises reacting the compound 4 with HFPO to form the following compound 5, and pyrolyzing the compound 5:

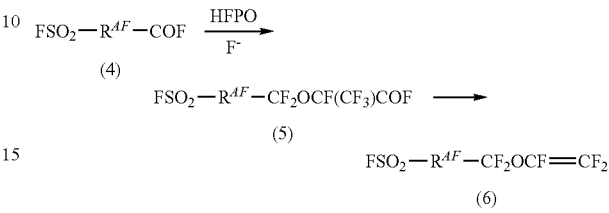

The present invention further provides a process for producing the following compound 6a, which comprises reacting HFPO with the compound 4a obtained by the above process to form the following compound 5a, and pyrolyzing the compound 5a:

$$FSO_2\text{-}Q^F\text{-}COF \quad (4a)$$

$$FSO_2\text{-}Q^F\text{-}CF_2OCF(CF_3)COF \quad (5a)$$

$$FSO_2\text{-}Q^F\text{-}CF_2OCF=CF_2 \quad (6a)$$

For example, the compound 4-1 can be converted into the compound 5-2 by a reaction represented by the following scheme. Further, the compound 4 wherein the terminal of the compound 5-2 or the like is —$CF(CF_3)COF$ can be converted into a compound 6-2 or the like having a —$CF=CF_2$ group at its molecular terminal by a pyrolytic reaction. The compound 6-2 having a polymerizable —$CF=CF_2$ group at the molecular terminal is useful as a monomer for preparation of an ion-exchange membrane:

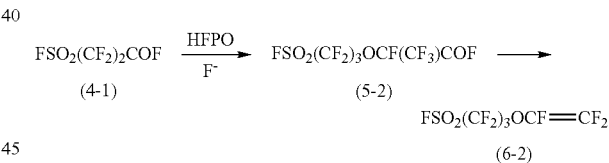

The pyrolytic reaction may be a gas phase pyrolytic reaction or such a reaction that an alkali hydroxide is reacted to obtain an alkali carboxylate, which is subjected to pyrolysis.

The reaction temperature for the gas phase pyrolytic reaction is preferably from 250 to 400° C., more preferably from 250 to 300° C. Further, the reaction temperature for the pyrolytic reaction of the alkali carboxylate is preferably from 150 to 350° C., more preferably from 200 to 280° C. When the reaction temperature for the gas phase pyrolytic reaction is 250° C. or higher or when the reaction temperature for the pyrolytic reaction of an alkali carboxylate is 150° C. or higher, such an advantage as excellent conversion ratio will be obtained. Further, when the reaction temperature for the gas phase pyrolytic reaction is 400° C. or lower or when the reaction temperature for the pyrolytic reaction of an alkali carboxylate is 350° C. or lower, generation of unintended pyrolysate will be suppressed.

With respect to the details of the gas phase pyrolytic reaction of a specific terminal fluorinated sulfonyl fluoride, the method as disclosed in WO02/44138 will be applicable.

According to the production process of the present invention, compounds having various structures can be produced efficiently with high yield under industrially advantageous conditions.

EXAMPLES

Now, the present invention will be described in detail with reference to Examples. In the following, gas chromatography will be referred to as GC, and gas chromatography mass spectrometry will be referred to as GC-MS. The purity determined from the peak area ratio of GC will be referred to as GC purity, the yield will be referred to as GC yield, and the yield determined from the peak area ratio of the NMR spectrum will be referred to as NMR yield. Tetramethylsilane will be referred to as TMS, and $CCl_2FCClF_2$ as R-113. The NMR spectrum data are shown as apparent chemical shifts (ppm). In the quantitative analysis by the $^{19}F$-NMR, $C_6F_6$ was used as the internal standard.

Example 1

Example for production of $FSO_2CF_2CF_2COF$

Example 1-1

Example for production of $Br(CH_2)_3OCOCF(CF_3)OCF_2CF(CF_3)OCF_2CF_2CF_3$ by esterification reaction $Br(CH_2)_3OH$ (21.7 g), methylene chloride (200 mL) and triethylamine (18.2 g) were put in a flask and stirred in an ice bath. $FCOCF(CF_3)_3OCF_2CF(CF_3)OCF_2CF_2CF_3$ (64.1 g) was added dropwise over a period of 60 minutes, while maintaining the internal temperature to be 10° C. or lower. After completion of the dropwise addition, stirring was carried out at room temperature for 2 hours, and the content was added to water (150 mL).

The obtained crude liquid was subjected to liquid separation, and the obtained lower layer was washed twice with an aqueous sodium hydrogen carbonate solution (60 mL) and twice with a saturated aqueous ammonium chloride solution (60 mL) and dried over magnesium sulfate, followed by filtration and concentration to obtain a crude liquid. The crude liquid was purified by silica gel column chromatography (eluent: mixed solvent comprising hexane (10): ethyl acetate (1)) to obtain the title compound (71.2 g, yield: 74%).

$^{1}H$-NMR (300.4 MHz, $CDCl_3$, TMS) δ: 2.27 (tt, J=5.9, 6.2 Hz, 2H), 3.45 (t, J=6.2 Hz, 2H), 4.50 (m, 1H), 4.60 (m, 1H).

$^{19}F$-NMR (282.7 MHz, $CDCl_3$, $CFCl_3$) δ: −78.4 to −85.1 (4F), −79.9 (3F), −81.3 (3F), −82.1 (3F), −129.1 (2F), −131.0 (1F), −144.5 (1F).

Example 1-2

Example for production of $NCS(CH_2)_3OCOCF(CF_3)OCF_2CF(CF_3)OCF_2CF_2CF_3$ by reaction with sulfur nucleophile Potassium thiocyanate (12.3 g) and acetone (150 mL) were put in a flask and stirred at room temperature. $Br(CH_2)_3OCOCF(CF_3)OCF_2CF(CF_3)OCF_2CF_2CF_3$ (71.2 g) obtained in Example 1-1 was charged thereinto. Then, reflux and stirring were carried out for 3 hours. The content was added to water (300 mL), extraction with t-butyl methyl ether (80 mL) was carried out four times, and the obtained organic layer was dried over magnesium sulfate, followed by filtration and concentration to obtain a crude liquid. The crude liquid was purified by silica gel column chromatography (eluent: mixed solvent comprising hexane (10): ethyl acetate (1)) to obtain the title compound (42.8 g, yield: 63%).

$^{1}H$-NMR (300.4 MHz, $CDCl_3$, TMS) δ: 2.30 (tt, J=6.0, 6.8 Hz, 2H), 3.03 (t, J=7.0 Hz, 2H), 4.52 (ddd, J=2.6, 6.0, 11.3 Hz, 1H), 4.61 (ddd, J=0.6, 6.0, 11.3 Hz, 1H).

$^{19}F$-NMR (282.7 MHz, $CDCl_3$, $CFCl_3$) δ: −77.7 to −79.1 (1F), −79.2 (3F), −80.5 to −80.9 (5F), −81.4 (3F), −83.1 to −84.1 (1F), −128.4 (2F), −130.2 (1F), −143.7 (1F).

IR (neat) 2159.6, 1785.8, 1240.3, 1147.5, 1035.0, 993.6 $cm^{-1}$.

Example 1-3

Example for production of $ClSO_2(CH_2)_3OCOCF(CF_3)OCF_2CF(CF_3)OCF_2CF_2CF_3$ by oxidation reaction In a flask equipped with a dry ice condenser, $NCS(CH_2)_3OCOCF(CF_3)OCF_2CF(CF_3)OCF_2CF_2CF_3$ (42.8 g) obtained in Example 1-2, water (45 mL) and acetonitrile (405 mL) were put and stirred at room temperature. Stirring was carried out at room temperature for 6 hours while bubbling chlorine gas thereinto. After the system was purged by nitrogen, the content was added to water (500 mL), extraction with t-butyl methyl ether (100 mL) was carried out four times, and the obtained organic layer was dried over magnesium sulfate, followed by filtration and concentration to obtain the title compound (35.4 g, yield: 77%). The product was subjected to the subsequent fluorine substitution reaction as it was without purification.

$^{1}H$-NMR (300.4 MHz, $CDCl_3$, TMS) δ: 2.50 (tt, J=6.2, 7.3 Hz, 2H), 3.74 (t, J=7.3 Hz, 2H), 4.50 to 4.66 (m, 2H).

$^{19}F$-NMR (282.7 MHz, $CDCl_3$, $CFCl_3$) δ: −78.4 to −85.0 (4F), −79.9 (3F), −81.2 (3F), −82.2 (3F), −129.1 (2F) −131.1 (1F), −144.5 (1F).

IR (neat) 1786.8, 1382.5, 1239.7, 1035.4, 993.9 $cm^{-1}$.

Example 1-4

Example for production of $FSO_2(CH_2)_3OCOCF(CF_3)OCF_2CF(CF_3)OCF_2CF_2CF_3$ by fluorine substitution reaction $ClSO_2(CH_2)_3OCOCF(CF_3)OCF_2CF(CF_3)OCF_2CF_2CF_3$ (35.4 g) obtained in Example 1-3, potassium hydrogen fluoride (8.9 g), water (80 mL) and acetonitrile (80 mL) were put in a flask and stirred at room temperature for 22 hours. The content was added to water (200 mL), extraction with t-butyl methyl ether (100 mL) was carried out four times, and the obtained organic layer was dried over magnesium sulfate, followed by filtration and concentration to obtain a crude liquid. The crude liquid was purified by silica gel column chromatography (eluent: mixed solvent comprising hexane (10): ethyl acetate (1)) to obtain the title compound (23.1 g, yield: 63%, GC purity: 95%).

$^{1}H$-NMR (300.4 MHz, $CDCl_3$, TMS) δ: 2.41 (tt, J=6.2, 7.3 Hz, 2H), 3.47 (dt, J=4.5, 7.3 Hz, 2H), 4.45 to 4.63 (m, 2H).

$^{19}F$-NMR (282.7 MHz, $CDCl_3$, $CFCl_3$) δ: 53.34 (1F), −78.4 to −85.0 (4F), −79.9 (3F), −81.2 (3F), −82.0 (3F), −129.1 (2F), −131.1 (1F), −144.5 (1F).

IR (neat) 1788.7, 1420.6, 1283.1, 1202.9, 1147.6, 1036.0, 994.0 cm$^{-1}$.

Example 1-5

Example for production of $FSO_2(CF_2)_3OCOCF(CF_3)OCF_2CF(CF_3)OCF_2CF_2CF_3$ by fluorination reaction Into a 500 mL autoclave made of nickel, R-113 (312 g) was added, stirred and then maintained at 25° C. At s the gas outlet of the autoclave, a cooler maintained at 20° C., a packed layer of NaF pellets and a cooler maintained at −10° C., were installed in series. Further, a liquid-returning line was installed to return a condensed liquid from the cooler maintained at −10° C. to the autoclave.

Nitrogen gas was blown into the autoclave at room temperature for 1 hour. Then, fluorine gas diluted to 20% by nitrogen gas (hereinafter referred to as 20% diluted fluorine gas) was blown at room temperature at a flow rate to 9.90 L/hr for 30 minutes, and then the internal pressure of the autoclave was elevated to 0.15 MPa, and the 20% diluted gas was blown further for 30 minutes. While maintaining the internal pressure of the reactor to be 0.15 MPa and blowing the 20% diluted fluorine gas at the same flow rate, a solution having the product (5 g) obtained in Example 1-4 dissolved in R-113 (100 g) was injected over a period of 3.0 hours.

Then, while maintaining the internal pressure of the reactor to be 0.15 MPa and blowing the 20% diluted fluorine gas at the same flow rate, 9 mL of a R-113 solution having a benzene concentration of 0.01 g/mL was injected while raising the temperature from 25° C. to 40° C., and the benzene solution inlet of the autoclave was closed and stirring was continued for 0.3 hour.

Then, while maintaining the internal pressure of the reactor to be 0.15 MPa and the internal temperature of the reactor to be 40° C., 6 mL of the above benzene solution was injected, the benzene solution inlet of the autoclave was closed, and stirring was continued for 0.3 hour. Further, the same operation was repeated one time. The total amount of benzene injected was 0.22 g, and the total amount of R-113 injected was 21 mL.

Further, stirring was continued 1 hour while blowing the 20% diluted fluorine gas at the same flow rate. Then, the pressure in the reactor was allowed to be normal pressure, and the nitrogen gas was blown for 1 hour. The product was analyzed by $^{19}$F-NMR and as a result, it was confirmed to contain the title compound with a yield of 65%.

$^{19}$F-NMR (282.7 MHz, CDCl$_3$, CFCl$_3$) δ: 46.3 (1F), −79.0 to −80.5 (4F), −82.0 (8F), −84.6 to −86.4 (3F), −108.9 (2F), −124.3 (2F), −130.2 (2F), −131.9 (1F), −145.4 (1F).

Example 1-6

Example for production of $FSO_2CF_2CF_2COF$ by decomposition reaction $FSO_2(CF_2)_3OCOCF(CF_3)OCF_2CF(CF_3)OCF_2CF_2CF_3$ (3.1 g) obtained in Example 1-5 was charged into a flask together with NaF powder (0.02 g) and heated at 140° C. for 10 hours in an oil bath with vigorous stirring. At the upper portion of the flask, a reflux condenser having the temperature maintained at 20° C. was installed. After cooling, a liquid sample (3.0 g) was recovered. As a result of the analysis by GC-MS, $CF_3CF_2CF_2OCF(CF_3)CF_2OCF(CF_3)COF$ and $FSO_2CF_2CF_2COF$ were confirmed to be the main products.

The NMR yield of the title compound was 71.2%, and the yield of $CF_3CF_2CF_2OCF(CF_3)CF_2OCF(CF_3)COF$ was 74.0%.

Example 1-7

Recycle of $CF_3CF_2CF_2OCF(CF_3)CF_2OCF(CF_3)COF$

As $CF_3CF_2CF_2OCF(CF_3)CF_2OCF(CF_3)COF$ of Example 1-1, the compound obtained in Example 1-6 is used to carry out the same reaction. Then, the same reactions as in Examples 1-2 to 1-6 are carried out to obtain $FSO_2CF_2CF_2COF$ and $CF_3CF_2CF_2OCF(CF_3)CF_2OCF(CF_3)COF$.

Example 1-8

Example for production of $FSO_2(CF_2)_3OCF=CF_2$ $FSO_2CF_2CF_2COF$ obtained in Example 1-6, CsF powder and diglyme are charged into an autoclave, and hexafluoropropene oxide is introduced with stirring under cooling with ice. Stirring is continued for 1 hour, and the content in the autoclave is distilled under reduced pressure to obtain $FSO_2CF_2CF_2OCF(CF_3)COF$.

$FSO_2(CF_2)_3OCF(CF_3)COF$ is added dropwise to a flask under cooling with ice, into which potassium bicarbonate and monoglyme are charged, with stirring. After completion of the dropwise addition, stirring is continued further for 30 minutes, and then the solvent is distilled off. Vacuum drying is further carried out to obtain $FSO_2(CF_2)_3OCF(CF_3)COOK$.

$FSO_2(CF_2)_3OCF(CF_3)COOK$ is heated at from 180 to 210° C. under reduced pressure, and generated gaseous product is collected in a trap cooled with liquid nitrogen to obtain $FSO_2(CF_2)_3OCF=CF_2$.

Example 2

Example for production of $FSO_2CF_2CF_2COF$

Example 2-1

Example for production of $BrCH_2CH_2COOCH_2CF(CF_3)OCF_2CF(CF_3)OCF_2CF_2CF_3$ by esterification reaction A mixture comprising trifluoroacetic anhydride (25.6 g) and 3-bromopropionic acid (17.9 g) was stirred at room temperature under a nitrogen stream for 1 hour. $CF_3CF_2CF_2OCF(CF_3)CF_2OCF(CF_3)CH_2OH$ (55.9 g) was added dropwise thereto while cooling with water so that the internal temperature would be maintained to be 30° C. or lower over a period of 30 minutes. 3 hours later, the reaction liquid was directly concentrated and purified by silica gel column chromatography (eluent: mixed solvent comprising hexane (10): ethyl acetate (1)) to obtain the title compound (54.6 g). The yield: 80%.

$^1$H-NMR (300.4 MHz, CDCl$_3$, TMS) δ: 3.01 (tm, J=6.8 Hz, 2H), 3.56 (t, J=6.8 Hz, 2H), 4.51 to 4.78 (m, 2H).

$^{19}$F-NMR (282.7 MHz, CDCl$_3$, CFCl$_3$) δ: −78.6 to −84.5 (4F), −79.9 (3F), −81.2 (3F), −82.8 (3F), −129.2 (2F), −133.7 (1F), −144.5 (1F).

Example 2-2

Example for production of $NCSCH_2CH_2COOCH_2CF(CF_3)OCF_2CF(CF_3)OCF_2CF_2CF_3$ by reaction with sulfur nucleophile Potassium thiocyanate (2.3 g) and acetone (25 mL) were put in a flask and stirred at room temperature. $BrCH_2CH_2COOCH_2CF(CF_3)OCF_2CF(CF_3)OCF_2CF_2CF_3$ (13.2 g) obtained in Example 2-1 was introduced thereinto. Then, reflux and stirring were carried out for 5 hours. The content was added to water (100 mL), extraction with t-butyl methyl ether (25 mL) was carried out four times, and the obtained organic layer was dried over magnesium sulfate, followed by filtration and concentration to obtain a crude liquid. The crude liquid was purified by silica gel column chromatography (eluent: mixed solvent comprising hexane (5): ethyl acetate (1)) to obtain the title compound (10.6 g). The yield: 75%.

$^1$H-NMR (300.4 MHz, CDCl$_3$, TMS) δ: 2.97 (tm, J=6.6 Hz, 2H), 3.20 (t, J=6.6 Hz, 2H), 4.53 to 4.80 (m, 2H).
$^{19}$F-NMR (282.7 MHz, CDCl$_3$, CFCl$_3$) δ: −78.6 to −84.4 (4F), −79.8 (3F), −81.2 (3F), −82.7 (3F), −129.1 (2F), −133.8 (1F), −144.4 (1F).
IR (neat) 2159.5, 1765.3, 1236.2, 1155.7, 993.5 cm$^{-1}$.

Example 2-3

Example for production of $ClSO_2CH_2CH_2COOCH_2CF(CF_3)OCF_2CF(CF_3)OCF_2CF_2CF_3$ by oxidation reaction In a flask equipped with a dry ice condenser, $NCSCH_2CH_2COOCH_2CF(CF_3)OCF_2CF(CF_3)OCF_2CF_2CF_3$ obtained in Example 2-2 (11.9 g), water (10 mL) and acetonitrile (90 mL) were put, and chlorine gas was bubbled with stirring at room temperature. Stirring was carried out in such a state at room temperature for 6 hours. After the system was purged by nitrogen, the content was added to water (300 mL), extraction with t-butyl methyl ether (50 mL) was carried out four times, and the obtained organic layer was dried over magnesium sulfate, followed by filtration and concentration to obtain the title compound (11.9 g). The yield: 91%. The product was subjected to the subsequent fluorination substitution reaction as it was without purification.

$^1$H-NMR (300.4 MHz, CDCl$_3$, TMS) δ: 3.13 (t, J=7.3 Hz, 2H), 4.00 (t, J=7.3 Hz, 2H), 4.55 to 4.82 (m, 2H).
$^{19}$F-NMR (282.7 MHz, CDCl$_3$, CFCl$_3$) δ: −78.5 to −84.4 (4F), −79.8 (3F), −81.2 (3F), −82.7 (3F), −129.2 (2F), −133.9 (1F), −144.5 (1F).
IR (neat) 1768.7, 1385.3, 1305.5, 1240.1, 1161.1, 993.5 cm$^{-1}$.

Example 2-4

Example for production of $FSO_2CH_2CH_2COOCH_2CF(CF_3)OCF_2CF(CF_3)OCF_2CF_2CF_3$ by fluorine substitution reaction $ClSO_2CH_2CH_2COOCH_2CF(CF_3)OCF_2CF(CF_3)OCF_2CF_2CF_3$ (16.0 g) obtained in Example 2-3, potassium hydrogen fluoride (3.9 g), water (50 mL) and acetonitrile (50 mL) were put in a flask and stirred at room temperature for 22 hours. The content was added to water (100 mL), extraction with t-butyl methyl ether (50 mL) was carried our four times, and the obtained organic layer was dried over magnesium sulfate, followed by filtration and concentration to obtain a crude liquid. The crude liquid was purified by silica gel column chromatography (eluent: mixed solvent comprising hexane (10): ethyl acetate (1)) to obtain the title compound (12.4 g). The yield: 80%.

$^1$H-NMR (300.4 MHz, CDCl$_3$, TMS) δ: 3.04 (dt, J=1.3, 7.3 Hz, 2H), 3.74 (dt, J=5.1, 7.3 Hz, 2H), 4.54 to 4.81 (m, 2H).
$^{19}$F-NMR (282.7 MHz, CDCl$_3$, CFCl$_3$) δ: 52.7 (1F), −78.6 to −84.5 (4F), −79.9 (3F), −81.3 (3F), −82.8 (3F), −129.2 (2F), −133.9 (1F), −144.5 (1F).
IR (neat) 1763.0, 1408.4, 1306.3, 1239.5, 1201.6, 1156.8, 993.5 cm$^{-1}$.

Example 2-5

Example for production of $FSO_2CF_2CF_2COOCF_2CF(CF_3)OCF_2CF(CF_3)OCF_2CF_2CF_3$ by fluorination reaction Using the same autoclave as in Example 1-5, the 20% diluted fluorine gas was blown at a flow rate of 7.77 L/hr at room temperature for 1 hour. Then, while blowing the 20% diluted fluorine gas at the same flow rate, a solution having the product (5 g) obtained in Example 2-4 dissolved in R-113 (50 g) was injected over a period of 3.1 hours.

Then, while blowing the 20% diluted fluorine gas at the same flow rate, the internal pressure of the autoclave was elevated to 0.15 MPa, 9 mL of a R-113 solution having a benzene concentration of 0.01 g/mL was injected while raising the temperature from 25° C. to 40° C., the benzene solution inlet of the autoclave was closed, and stirring was continued for 0.3 hour.

Then, while maintaining the internal pressure of the reactor to be 0.15 MPa and the internal temperature of the reactor to be 40° C., 6 mL of the above benzene solution was injected, the benzene solution inlet of the autoclave was closed, and stirring was continued for 0.3 hour. The same operation was further repeated one time. The total amount of benzene injected was 0.21 g, and the total amount of R-113 injected was 21 mL.

Further, stirring was continued for 1 hour while blowing the 20% diluted fluorine gas at the same flow rate. Then, the internal pressure of the reactor was allowed to be normal pressure, and nitrogen gas was blown for 1 hour. The product was analyzed by $^{19}$F-NMR and as a result, it was confirmed to contain the title compound with a yield of 57%.

$^{19}$F-NMR (282.7 MHz, CDCl$_3$, CFCl$_3$) δ: 46.3 (1F), −79.0 to −83.8 (12F), −84.6 to −86.4 (3F), −108.9 (2F), −117.2 (2F), −130.2 (2F), −145.4 (2F).

Example 2-6

Example for production of $FSO_2CF_2CF_2COF$ by decomposition reaction $FSO_2CF_2CF_2COOCF_2CF(CF_3)OCF_2CF(CF_3)OCF_2CF_2CF_3$ (3.6 g) obtained in Example 2-5 was charged into a flask together with NaF powder (0.02 g) and heated at 140° C. for 10 hours in an oil bath with vigorous stirring. At the upper portion of the flask, a reflux condenser having the temperature maintained at 20° C. was installed. After cooling, a liquid sample (3.4 g) was recovered. As a result of the analysis by GC-MS, $CF_3CF_2CF_2OCF(CF_3)CF_2OCF(CF_3)COF$ and the title compound were confirmed as the main products. The NMR yield of the title compound was 70.9%, and the yield of $CF_3CF_2CF_2OCF(CF_3)CF_2OCF(CF_3)COF$ was 72.0%.

Example 2-7

Recycle of $CF_3CF_2CF_2OCF(CF_3)CF_2OCF(CF_3)COF$ $CF_3CF_2CF_2OCF(CF_3)CF_2OCF(CF_3)COF$ obtained in Example 2-6 is reacted with methanol in an equimolar amount in the presence of sodium fluoride to obtain $CF_3CF_2CF_2OCF(CF_3)CF_2OCF(CF_3)COOCH_3$. The obtained $CF_3CF_2CF_2OCF(CF_3)CF_2OCF(CF_3)COOCH_3$ is reacted with sodium borohydride in 2-propanol to obtain $CF_3CF_2CF_2OCF(CF_3)CF_2OCF(CF_3)CH_2OH$. The obtained $CF_3CF_2CF_2OCF(CF_3)CF_2OCF(CF_3)CH_2OH$ is employed as the compound in Example 2-1 to carry out the same reaction. Further, the same reactions as in Examples 2-2 to 2-6 are carried out to obtain $FSO_2CF_2CF_2COF$ and $CF_3CF_2CF_2OCF(CF_3)CF_2OCF(CF_3)COF$.

INDUSTRIAL APPLICABILITY

According to the production process of the present invention, a novel process to produce sulfonyl fluoride compounds having various structures from easily available materials at a low cost is provided. The process of the present invention, in which a product can be recycled, is economically advantageous and is an industrially useful process which reduces the amount of waste.

The entire disclosure of Japanese Patent Application No. 2003-271071 filed on Jul. 4, 2003 including specification, claims, and summary is incorporated herein by reference in its entirety.

What is claimed is:

1. A process for producing a fluorinated sulfonyl fluoride represented by the following formula (4), which comprises oxidizing a compound represented by the following formula (1) with an oxidizing agent comprising a halogen atom to obtain a compound represented by the following formula (2), and in a case that X in the compound represented by the formula (2) is a fluorine atom, reacting the compound with fluorine in a liquid phase as it is, to obtain a compound represented by the following formula (3), and in a case that X in the compound represented by the formula (2) is a halogen atom other than a fluorine atom, converting X into a fluorine atom, and then reacting the obtained compound with fluorine in a liquid phase to obtain a compound represented by the following formula (3), and then decomposing the compound represented by the formula (3):

$$Y-S-R^A-E-R^B \quad (1)$$

$$XSO_2-R^A-E-R^B \quad (2)$$

$$FSO_2-R^{AF}-E^F-R^{BF} \quad (3)$$

$$FSO_2-R^{AF}-COF \quad (4)$$

wherein $R^A$ is a bivalent organic group;
$R^B$ is a monovalent organic group;
E is $-CH_2OCO-$, and the carbon atom constituting the keto group in E is bonded to $R^A$ or $R^B$;
Y is a hydrogen atom, a monovalent organic group or a $-SO_3M$ group (wherein M is an alkali metal atom);
X is a halogen atom;
$R^{AF}$ is the same group as $R^A$ or a bivalent organic group having $R^A$ fluorinated;
$R^{BF}$ is the same group as $R^B$ or a monovalent organic group having $R^B$ fluorinated; and
$E^F$ is $-CF_2OCO-$, and the carbon atom constituting the keto group in $E^F$ is bonded to $R^{AF}$ or $R^{BF}$.

2. The process according to claim 1, wherein the reaction with fluorine in a liquid phase is a perfluorination reaction.

3. The process according to claim 1, wherein X is a chlorine atom.

4. A process for producing a fluorinated vinyl compound represented by the following formula (6), which comprises adding hexafluoropropylene oxide to the compound represented by the following formula (4) obtained by the process as defined in claim 1, to obtain a compound represented by the following formula (5), and subjecting the compound represented by the formula (5) to a decomposition reaction:

$$FSO_2-R^{AF}-COF \quad (4)$$

$$FSO_2-R^{AF}-CF_2OCF(CF_3)COF \quad (5)$$

$$FSO_2-R^{AF}-CF_2OCF=CF_2 \quad (6)$$

wherein $R^{AF}$ is as defined above.

5. A process for producing a compound represented by the following formula (4a), which comprises oxidizing a compound represented by the following formula (1a) with an oxidizing agent comprising a chlorine atom or a bromine atom to obtain a compound represented by the following formula (2a), converting the $X^A S0_2-$ group in the compound represented by the formula (2a) into a $FSO_2$- group to obtain a compound represented by the following formula (2aF), reacting the compound represented by the formula (2aF) with fluorine in a liquid phase for perfluorination to obtain a compound represented by the following formula (3a), and further decomposing the compound represented by the formula (3a):

$$NCS-Q-CH_2OCO-R^{BF1} \quad (1a)$$

$$X^A SO_2-Q-CH_2OCO-R^{BF1} \quad (2a)$$

$$FSO_2-Q-CH_2OCO-R^{BF1} \quad (2aF)$$

$$FSO_2-Q^F-CF_2OCO-R^{BF1} \quad (3a)$$

$$FSO_2-Q^F-COF \quad (4a)$$

wherein Q is an alkylene group, $Q^F$ is a group having Q perfluorinated and represents a perfluoroalkylene group, $X^A$ is a chlorine atom or a bromine atom, $R^{BF1}$ is a $C_{1-20}$ perfluoroalkyl group or a $C_{1-20}$ perfluoroalkyl group having an etheric oxygen atom.

6. The process according to claim 5, wherein oxidation of the compound represented by the formula (1a) is carried out by reacting it with chlorine in a solvent comprising water to obtain a compound represented by the formula (2a) wherein $X^A$ is a chlorine atom, and the compound represented by the formula (2a) is reacted with potassium fluoride in a liquid phase to convert it into the compound represented by the formula (2aF).

7. The process according to claim 5, wherein Q is a $C_{2-10}$ alkylene group, and $Q^F$ is a $C_{2-10}$ perfluoroalkylene group.

8. The process according to claim 5, wherein Q is a $C_{2-10}$ linear alkylene group, and $Q^F$ is a $C_{2-10}$ linear perfluoroalkylene group.

9. A process for producing a compound represented by the following formula (6a), which comprises adding hexafluoropropylene oxide to the compound represented by the following formula (4a) obtained by the process as defined in claim 5, to obtain a compound represented by the following formula (5a), and subjecting the compound represented by the formula (5a) to a decomposition reaction:

$$FSO_2-Q^F-COF \quad (4a)$$

$$FSO_2-Q^F-CF_2OCF(CF_3)COF \quad (5a)$$

$$FSO_2-Q^F-CF_2OCF=CF_2 \quad (6a)$$

wherein $Q^F$ is as defined above.

10. The process according to claim 1, wherein X is a fluorine atom.

* * * * *